United States Patent
Golarits et al.

(10) Patent No.: US 9,999,716 B2
(45) Date of Patent: Jun. 19, 2018

(54) ACUTE RENAL REPLACEMENT THERAPY APPARATUS

(71) Applicant: B. BRAUN AVITUM AG, Melsungen (DE)

(72) Inventors: István Golarits, Budapest (HU); Botond Tényi, Budakalász (HU)

(73) Assignee: B. BRAUN AVITUM AG, Melsungen (DE)

( * ) Notice: Subject to any disclaimer, the term of this patent is extended or adjusted under 35 U.S.C. 154(b) by 282 days.

(21) Appl. No.: 14/870,613

(22) Filed: Sep. 30, 2015

(65) Prior Publication Data
US 2016/0121037 A1   May 5, 2016

(30) Foreign Application Priority Data
Oct. 29, 2014   (EP) .................................... 14190925

(51) Int. Cl.
*A61M 37/00* (2006.01)
*A61M 1/34* (2006.01)
(Continued)

(52) U.S. Cl.
CPC ............ *A61M 1/3451* (2014.02); *A61M 1/16* (2013.01); *A61M 1/1615* (2014.02);
(Continued)

(58) Field of Classification Search
CPC .............. A61M 1/3451; A61M 1/1615; A61M 1/1643; A61M 1/1647; A61M 1/3403;
(Continued)

(56) References Cited

U.S. PATENT DOCUMENTS

| | | |
|---|---|---|
| 2005/0085760 A1 | 4/2005 | Ware |
| 2011/0017667 A1 | 1/2011 | DeImage |
| 2014/0074008 A1 | 3/2014 | Fontanazzi et al. |

FOREIGN PATENT DOCUMENTS

| | | |
|---|---|---|
| CN | 103547299 A | 1/2014 |
| EP | 0611228 | 8/1994 |

(Continued)

OTHER PUBLICATIONS

European Search Report dated Apr. 16, 2015 in European Application No. 14190925.9.
(Continued)

*Primary Examiner* — Philip R Wiest
(74) *Attorney, Agent, or Firm* — RatnerPrestia

(57) ABSTRACT

A renal therapy apparatus including at least two feedback controls is disclosed. Each control includes an estimated volume calculator to calculate an estimated volume based on a set flow, a comparator to compare the estimated volume with a measured volume, a volume deviation determining means to determine a volume deviation based on the comparison, a correction calculator to calculate a correction based on the volume deviation, a flow control generator to generate a flow control signal based on the calculated correction amount and the set flow, and a feedback control output to output the controlled flow control signal to a pump associated with each feedback control. A flow correction distributor includes an input to receive correction signals from the correction calculator, a limited correction signal calculator to calculate a limited correction signal for the input correction required signals, and an output to output each calculated limited correction signal to the feedback control from which its underlying correction required signal has been received.

9 Claims, 2 Drawing Sheets

(51) Int. Cl.
   *A61M 1/16* (2006.01)
   *A61M 1/36* (2006.01)
(52) U.S. Cl.
   CPC ........ *A61M 1/1643* (2014.02); *A61M 1/1647* (2014.02); *A61M 1/34* (2013.01); *A61M 1/341* (2014.02); *A61M 1/342* (2013.01); *A61M 1/3403* (2014.02); *A61M 1/3441* (2013.01); *A61M 1/3607* (2014.02); *A61M 1/3663* (2013.01); *A61M 2205/3331* (2013.01); *A61M 2205/3334* (2013.01); *A61M 2205/3379* (2013.01); *A61M 2205/3393* (2013.01); *A61M 2205/50* (2013.01)
(58) Field of Classification Search
   CPC ...... A61M 1/341; A61M 1/3607; A61M 1/16; A61M 1/34; A61M 1/342; A61M 1/3441; A61M 1/3663; A61M 2205/3331; A61M 2205/3334; A61M 2205/3379; A61M 2205/3393; A61M 2205/50
   See application file for complete search history.

(56) References Cited

FOREIGN PATENT DOCUMENTS

| | | |
|---|---|---|
| EP | 2644215 | 10/2013 |
| WO | 2012127298 | 9/2012 |

OTHER PUBLICATIONS

Chinese Office Action for Chinese Application No. 201510646508.3, dated Nov. 3, 2017 with translation, 10 pages.

ACUTE RENAL REPLACEMENT THERAPY APPARATUS

CROSS REFERENCE TO RELATED APPLICATIONS

This application claims priority to European application EP 14190925.9 filed Oct. 29, 2014, the contents of such application being incorporated by reference herein.

FIELD OF THE INVENTION

The invention relates generally to blood filtration and to continuous renal replacement therapy (CRRT). More specifically, the invention relates to monitoring fluid loss and fluid replacement during CRRT therapy and automatically controlling fluid flow rates.

BACKGROUND OF THE INVENTION

Many patients suffering from acute renal failure are treated with various forms of hemofiltration, known generally as Continuous Renal Replacement Therapy (CRRT). In hemofiltration, a patient's blood is routed into an extracorporeal circuit and led under pressure through a blood filter, or hemofilter. The hemofilter contains a semi-permeable membrane that separates water and waste solutes from the main flow of blood. The filtered blood is then returned to the patient. Hemodialysis, as another form of renal replacement therapy, differs from hemofiltration in that a dialysate fluid is made to flow along a side of the semi-permeable membrane opposite to the side where blood flows. Concentration gradients across the membrane encourage the migration of unwanted solutes out of the blood into the dialysate by osmosis. Hemodialysis usually can only be applied for a few hours per day, and as such, is more restrictive and sometimes less effective than pure hemofiltration. However, hemodialysis can be combined with hemofiltration to provide more complex blood filtration therapies.

Typically, a hemofilter or artificial kidney is used during CRRT therapy. The artificial kidney may be formed of hollow-fibers or closely separated plates, and is connected to a patient's bloodstream through an extracorporeal circuit. The supply from and the return to the blood of the patient can be made via two venous accesses, using a blood pump to provide the driving force for the transport of blood from the patient into the artificial kidney and back to the patient. An access providing the supply of blood to the artificial kidney can alternatively be made through an artery, and the return of the blood to the patient can be made through a vein. In this case, the arterial blood pressure provides the driving force to transport the blood, and blood pumps are not necessarily mandatory. However, a pump provides better control of blood flow, and renal replacement therapies using blood pumps are preferred.

Mimicking the natural filtering function of a kidney over a semipermeable membrane leads to a considerable loss of fluid from the blood, which is removed as the filtrate in the artificial kidney. Every liter of filtrate fluid removed in the artificial kidney contains a large fraction of the molecules that are dissolved in the plasma. The fraction of molecules that pass the semipermeable membrane depends on the chemical characteristics of the molecules, the structure of the membrane, and the transmembrane pressure (TMP). In order to keep the blood volume of the patient constant, a substitution fluid is usually added in approximately the same amount to the bloodstream in the extracorporeal circuit. The substitution fluid commonly used is conventional infusion fluid comprising a physiological saline solution.

Performing CRRT usually requires the use of a CRRT machine for controlling blood flow through the extracorporeal circuit. Typically, a CRRT machine draws blood from a patient through an access line using a blood pump (e.g., a peristaltic pump), and returns the blood to the patient through a return line. The flow rate of the blood pump, the design of the artificial kidney, and the type of CRRT therapy used determine the fluid loss rate from the bloodstream through the filter.

Pressure sensors throughout the extracorporeal circuit may be used to sense and alarm fluid flow at various points. For example, an access line pressure sensor may sense pressure of blood entering the extracorporeal circuit, and generate an alarm in the event the sensor senses an out-of-range condition. Similarly, a return line pressure sensor may also sense and transmit pressure signals and generate alarms.

Pressure sensors placed before the hemofilter, in the filtrate outflow, and in the return line provide measurements needed to calculate TMP or the pressure drop (PD) in blood flowing through the artificial kidney.

During therapy, dialysate fluid flows into the dialysate compartment of the artificial kidney, and a filtration pump is used to remove used dialysate (or effluent) from the blood circulating through the artificial kidney. The effluent is collected inside a filtration container and may also be weighed to monitor fluid loss.

A procedural safeguard may be provided where plasma fluid lost through the artificial kidney can be compared to the amount of substitution fluid added to the extracorporeal circuit. The difference yielded by this comparison is the total fluid loss (or gain) TFL. In most therapies, TFL is ideally maintained at zero, i.e., no net loss of vital fluids.

A common technique for detecting TFL in CRRT machines: direct regulation and differential regulation. Direct regulation calculates TFL by reading weight values for both filtration fluid and substitution fluid at regular time intervals. The weighed value of filtration fluid is compared to an expected value of filtration fluid calculated by the CRRT machine. Any difference between weighed and expected values yields a correction signal that adjusts filtration flow rate caused by the filtration pump. Similarly, the weighed value of substitution fluid is compared to an expected value of substitution fluid calculated by the CRRT machine. Any difference between weighed and expected values yields a correction signal that adjusts substitution flow rate caused by the substitution pump. In this manner, the performance of each pump is individually controlled to meet predetermined performance criteria. Differential regulation calculates TFL by continuously measuring weight change of filtration and substitution fluids over the same time period. The change in filtration fluid in a single period is subtracted from the change in substitution fluid over the same time period, yielding a value for TFL. This value is compared to a predetermined value of expected TFL. If the comparison yields a difference, a correction signal is generated to balance the system, i.e., to govern one or both of the filtration and substitution pump flow rates and cause TFL to converge toward zero or some other desired value.

Both direct and differential regulation schemes have limitations. When regulation cannot achieve a desired balance, an alarm may be generated. In state-of-the-art net fluid removal (NFR) control systems, upon error compensation, NFR rate changes are not continuously, i.e. both short-term and within long periods over e.g. several hours, limited to a low level which is not harmful for the patient.

SUMMARY OF THE INVENTION

In view of the above, an object of the invention resides in providing a blood treatment apparatus capable of, in case of an error compensation and/or in case of a fluid loss rate deviation correction, limiting a net fluid rate change to a level low enough to ensure gentle and harmless operation for the patient.

According to aspects of the invention, this object is accomplished by an acute renal replacement therapy apparatus, a flow correction distribution device, an acute renal replacement therapy apparatus, and a flow correction distribution method as defined in the claims. Advantageous further developments of the invention are subject of the accompanying dependent claims.

Thus, according to a first aspect of the invention, an acute renal replacement therapy apparatus is comprises at least two feedback control means, each including an estimated volume calculation means arranged to calculate an estimated volume based on a set flow; a comparing means arranged to compare the estimated volume with a measured flow; a volume deviation determining means arranged to determine a volume deviation based on the result of the comparison; a correction calculation means arranged to calculate a correction amount based on the determined volume deviation; a flow control generation means arranged to generate a controlled flow control signal based on the calculated correction amount and the set flow; and a feedback control output means arranged to output the controlled flow control signal to a pump individually associated with each feedback control means and forwarding fluid from a fluid source and/or pulling fluid into a fluid sink; and a flow correction distribution means including an input means arranged to receive correction required signals calculated by and output from the correction calculation means in each of the at least two feedback control means; a limited correction signal calculation means arranged to calculate a limited correction signal for each of the correction required signals; and an output means arranged to output each calculated limited correction signal to the feedback control means from which its underlying correction required signal has been received.

Preferably, said flow correction distribution means comprises a weighted distribution logic means including a correction required signal receiving means arranged to receive at least two correction required signals from said input means, and a maximum correction amount determining means arranged to determine a weighted maximum correction amount for each of the at least two correction required signals, wherein the flow correction distribution means is arranged to apply the weighted maximum correction amount determined by the weight distribution logic means to the correction required signal it has been determined for, and to output the corrected signal as the limited correction signal.

Further preferably, the flow correction distribution means comprises a stability detector logic means arranged to receive at least two flow stability indication signals and to output a correction stability signal; and a switching means arranged to receive the correction stability signal from said stability detector logic means and to switch, depending on the state of the correction stability signal, between a first state yielding a first net fluid removal rate for a stable condition and a second state yielding a second net fluid removal rate for an unstable condition.

Further preferably, said first net fluid removal rate is lower than said second net fluid removal rate, and the net fluid removal rate set by said switching means is input into the weighted distribution logic means as a total net fluid removal rate change indicating an applicable total correction limit.

Also preferably, the weight distribution logic means is arranged to calculate the maximum correction amount for at least one correction required signal by dividing said total correction limit by a sum of correction requests.

Further preferably, the at least one correction required signal is an effluent correction required signal.

In addition preferably, the acute renal replacement therapy apparatus further includes a net fluid removal rate calculation means arranged to receive at least a first and a second measured volume signal and to calculate a measured net fluid removal rate volume signal based on the input first and second measured volumes; a net fluid removal deviation calculation means arranged to receive said measured net fluid removal rate volume signal and an estimated net fluid removal rate signal and to calculate a net fluid removal deviation signal based on said input measured net fluid removal rate volume signal and said input estimated net fluid removal rate signal; and a net fluid removal rate comparing means arranged to receive the calculated net fluid removal deviation signal, to compare the calculated net fluid removal deviation signal with a threshold value yielding a net fluid removal rate alarm limit, and to trigger a high net fluid removal rate alarm or a low net fluid removal alarm when the obtained net fluid removal deviation is higher than said net fluid removal rate alarm limit.

Also preferably, the apparatus is arranged to be set into a safety state when the high or low net fluid removal alarm is triggered.

In addition preferably, a first one of said at least two feedback control means is a substitution feedback control means including: as said estimated volume calculation means, an estimated substitution volume calculation means arranged to calculate an estimated substitution volume based on a set substitution flow; as said comparing means, a first comparing means arranged to compare the estimated substitution volume with a measured substitution volume; as said volume deviation means, a substitution volume deviation determining means arranged to determine a substitution volume deviation based on the result of the comparison; as said correction calculation means, a substitution correction calculation means arranged to calculate a substitution correction based on the determined substitution volume deviation; as said flow control generation means, a substitution flow control generation means arranged to generate a controlled substitution flow control signal based on the calculated substitution correction and the set substitution flow; and as said feedback control output means, a first output means arranged to output the controlled substitution flow control signal to a substitution pump forwarding substitution fluid from a substitution fluid source; a second one of said at least two feedback control means is an effluent feedback control means including: as said estimated volume calculation means, an estimated effluent volume calculation means arranged to calculate an estimated effluent volume based on a calculated (or set) effluent flow; as said comparing means, a second comparing means arranged compare the estimated effluent volume with a measured effluent volume; as said volume deviation means, an effluent volume deviation determining means arranged to determine an effluent volume deviation based on the result of the comparison; as said correction calculation means, an effluent correction calculation means arranged to calculate an effluent correction based on the determined effluent volume deviation; as said flow control generation means, an effluent flow control generation means arranged to generate a controlled effluent flow control signal based on the calculated effluent correction and the set effluent flow; and as said feedback control output means, a second output means arranged to output the controlled effluent flow control signal to an effluent pump forwarding effluent fluid into an effluent fluid sink; and in said flow correction distribution means: said input means is arranged to receive, as said required correction signals, a required substitution correction signal from the substitution correction calculation means and a required effluent correction signal from the effluent correction calculation means; said limited correction signal calculation means is arranged to calculate, as said limited correction signal for each of the input correction signals, a limited substitution correction signal and a limited effluent correction signal based on the required substitution correction signal and the required effluent correction signal; and said output means is arranged to output, as said each calculated limited correction signal, the calculated limited substitution correction signal to the substitution feedback control means and to output the calculated limited effluent correction signal to the effluent feedback control means.

According to a second aspect of the invention, a flow correction distribution means for use in an acute renal replacement therapy apparatus, wherein said acute renal replacement therapy apparatus comprises at least an effluent pump and one or more substitution pumps and being arranged to control flow rates delivered by each pump based on a measured fluid weight change and a calculated estimated delivery volume, and to automatically eliminate a pump delivery deviation using flow rate feedback control associated to each of said at least an effluent pump and one or more substitution pumps, includes an input means arranged to receive correction required signals calculated by and output from a correction calculation means in each flow rate feedback control; a limited correction signal calculation means arranged to calculate a limited correction signal for each of the received correction required signals; and an output means arranged to output each calculated limited correction signal to the flow rate feedback control from which its underlying correction required signal has been received.

According to a third aspect of the invention, an acute renal replacement therapy method includes the steps of: in each of at least two feedback control means, calculating an estimated volume based on a set flow; comparing the estimated volume with a measured volume; determining a volume deviation based on the result of the comparison; calculating a correction amount based on the determined volume deviation; generating a controlled flow control signal based on the calculated correction amount and the set flow; and outputting the controlled flow control signal to a pump individually associated with each feedback control means and forwarding fluid from a fluid source and/or pulling fluid into a fluid sink; and in a flow correction distribution means: inputting correction required signals calculated and output by the maximum correction amount calculation step in each of the at least two feedback control means; calculating a limited correction signal for each of the input correction required signals; and outputting each calculated limited correction signal to the feedback control means from which its underlying correction required signal has been received.

Preferably, in a weighted distribution logic means comprised of said flow correction distribution means, the steps of: receiving at least two correction required signals; determining a weighted maximum correction amount for each of the at least two correction required signals; applying the determined weighted maximum correction amount to the correction required signal it has been determined for; and outputting the corrected signal as the limited correction signal are carried out.

Preferably, in said flow correction distribution means, the steps of: logically processing at least two flow stability indication signals and outputting a correction stability signal; and switching, depending on the state of the correction stability signal, between a first net fluid removal rate correction limit for a stable condition and a second net fluid removal rate correction limit for an unstable condition, are carried out. Where the stable and unstable conditions may comprise further sub-states for finer resolution.

Further preferably, said first net fluid removal rate correction limit is lower than said second net fluid removal rate correction limit, and a the step of inputting the net fluid removal rate set in said switching step into the weighted distribution logic means as a total net fluid removal rate change indicating an applicable total correction limit is carried out.

Also preferably, a step of calculating the maximum correction amount for at least one correction required signal by dividing said total correction limit by a sum of correction requests is included.

Still preferably, the at least one correction required signal is an effluent correction required signal.

Also preferably, the steps of: inputting at least a first and a second measured volume signal and calculating a measured net fluid removal volume signal based on the input first and second measured volumes; calculating a net fluid removal deviation signal based on said input measured net fluid removal rate volume signal and said input estimated net fluid removal rate signal; comparing the calculated net fluid removal deviation signal with a threshold value yielding a net fluid removal rate alarm limit; and triggering a high net fluid removal rate alarm or a low net fluid removal alarm when the obtained net fluid removal deviation is higher than said net fluid removal rate alarm limit are carried out.

Further preferably, a step of setting the apparatus into a safety state when the high or low net fluid removal alarm is triggered is carried out.

More preferably, the acute renal replacement therapy method may include the steps of: in a substitution feedback control means as a first one of said at least two feedback control means: calculating an estimated substitution volume based on a set substitution flow; comparing the estimated substitution volume with a measured substitution volume; determining a substitution volume deviation based on the result of the comparison; calculating a substitution correction based on the determined substitution volume deviation; generating a controlled substitution flow control signal based on the calculated substitution correction and the set substitution flow; and outputting the controlled substitution flow control signal to a substitution pump forwarding substitution fluid from a substitution fluid source; in an effluent feedback control means as a second one of said at least two feedback control means: calculating an estimated effluent volume based on a set effluent flow; comparing the estimated effluent volume with a measured effluent volume; determining an effluent volume deviation based on the result of the comparison; calculating an effluent correction based on the determined effluent volume deviation; generating a controlled effluent flow control signal based on the calculated effluent correction and the set effluent flow; and outputting the controlled effluent flow control signal to an effluent pump forwarding effluent fluid into an effluent fluid sink; and in said flow correction distribution means: inputting, as said required correction signals, a required substitution correction signal obtained in the substitution correction calculation step and a required effluent correction signal obtained in the effluent correction calculation step; calculating, as said limited correction signal for each of the input correction signals, a limited substitution correction signal and a limited effluent correction signal based on the required substitution correction signal and the required effluent correction signal; and outputting, as said each calculated limited correction signal, the calculated limited substitution correction signal to the substitution feedback control means and outputting the calculated limited effluent correction signal to the effluent feedback control means.

According to a fourth aspect of the invention, a flow correction distribution method for use in an acute renal replacement therapy apparatus, wherein acute renal replacement therapy apparatus comprises at least an effluent pump and one or more substitution pumps and being arranged to control flow rates delivered by each pump based on a measured fluid weight change and a calculated estimated delivery volume, and to automatically eliminate a pump delivery deviation using flow rate feedback control associated to each of said at least an effluent pump and one or more substitution pumps, includes the steps of: inputting correction required signals calculated by and output from a correction calculation step in each flow rate feedback control; calculating a limited correction signal for each of the input correction required signals; and outputting each calculated limited correction signal to the flow rate feedback control from which its underlying correction required signal has been received.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
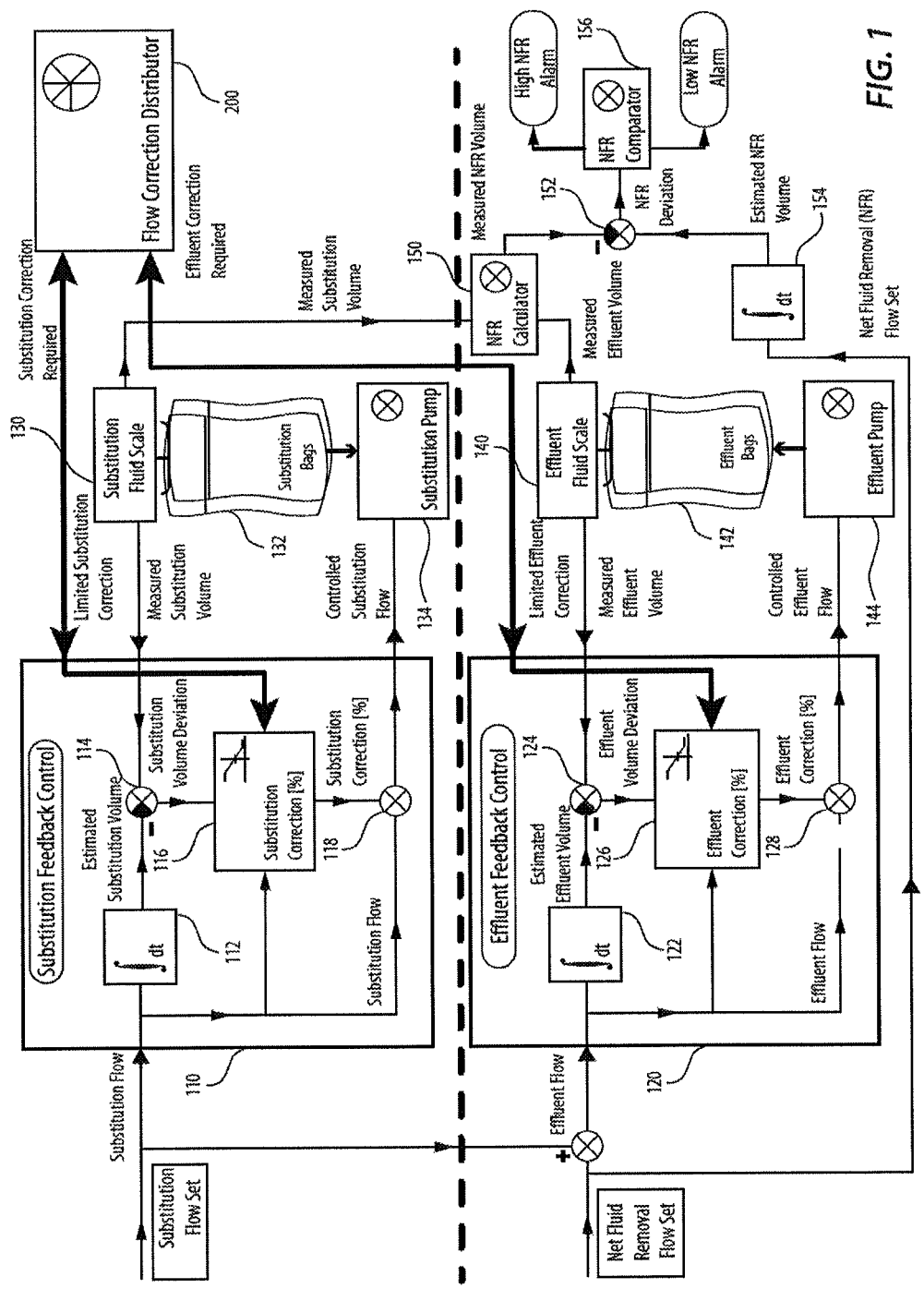
FIG. 1 schematically depicts a pump flow control in an applicable acute renal replacement therapy apparatus using a flow correction distributor device according to a preferred embodiment.

Generally referring to FIG. 1, during an acute renal replacement therapy, one of the most important tasks is to prevent, or compensate for, the weight loss of the patient by controlling a target net fluid removal (NFR) rate. To this effect, an acute renal replacement therapy apparatus contains at least an effluent pump, one or more substitution pumps, a dialysis pump, and optionally a citrate pump.

FIG. 1 schematically depicts a pump flow control in an applicable acute renal replacement therapy apparatus according to a preferred embodiment of the invention. In the shown setup, each pump (except the blood pump) is responsible for delivering fluids from/to bags during a blood treatment procedure. The weight gain/weight loss of bags (hereinafter bag weight change) is measured with an appropriate scale (weight measuring mechanism).

An estimated delivered fluid volume (hereinafter delivery volume) is calculated from a set flow rate (a user defined rate) and time. The substitution, dialysis and citrate flow rates are user defined set values, while the effluent flow rate is the sum of the formerly mentioned flow rates, increased by the user defined net fluid removal (NFR) rate.

For each pump the measured bag weight change and the estimated delivery volume is compared, and the pump delivery deviation is eliminated automatically by a flow rate feed-back control associated to the respective pump. The net fluid removal (NFR) volume is the result of the fluid flows applied during the therapy, which should be equal to the weight loss of the patient. This means that the NFR deviation will be equal to the sum of pump delivery deviations for each fluid pump. By correcting the fluid pump delivery deviations independently for each pump, the NFR deviation will be eliminated as well. A measured NFR volume (which is called so here because its value is based on actually measured volumes) is calculated from measured fluid volumes. The measured NFR volume is compared to an estimated NFR volume, which is an expected value determined using e.g. a form of integral technique. If the fluid pump delivery deviations are not corrected properly and thus the obtained NFR deviation is higher than an NFR alarm limit, the system triggers an NFR alarm and sets the system into a safety state. This control ensures a more precise renal dose, and bag changes are more predictable.

More specifically, while it is understood that symbols and characteristics shown in the attached figures immediately and per se render and exhibit to a skilled person the technical functionality involved and, thus, a particular description and/or details of such functionality may conveniently be omitted It is further understood that means described hereinafter can be part of internal electronics of the apparatus and as such comprise software routines and hardware including at least e.g. a printed board, a microprocessor, RAM, ROM, logic circuits, I/O configurations, active and passive elements, active and passive components, electronic switches and the like in a form and a layout suitable to process signals, variable, values, amounts, physical quantities and the like input and/or applied thereto. Such sections and/or electronics can be provided as pluggable modules, on mainboards to be installed in situ, or otherwise assembled to functional units, and be accommodated in one or more separate housings or placed internally on sort of a chassis placed in a common casing, and interconnected by leads or harnesses, or otherwise networked. Other means mentioned hereinafter may further and as need be comprise sort of standalone units, such as pumps, scales, hardware switches, displays, containers, fluid passages and the like.

According to the schematic shown in FIG. 1, a substitution flow and a net fluid removal (NFR) flow are set by e.g. a user or an external control unit of the acute renal replacement therapy apparatus. While the set substitution flow is input as such to a substitution flow feedback control section or means 110, an effluent flow to be input to an effluent feedback control section or means 120 is a combination of the set NFR flow and the set substitution flow which are added together, or combined, prior to entering into the effluent feedback control means 120.

Each substitution and effluent feedback control means 110, 120 includes a calculation means 112, 122 integrally processing the input substitution flow signal and effluent flow signal, respectively, to calculate an estimated substitution volume and an estimated effluent volume, respectively.

The estimated substitution volume is then compared 114 to a measured substitution volume obtained and input from a substitution fluid scale 130 weighing substitution fluid retrieved from e.g. a substitution fluid bag 132 as a substitution fluid source by the operation of a substitution pump

134. The comparison can for example be rendered by a comparator, an adder, or suitable other logic involving arithmetic operations and incorporated to this effect in some chip or microprocessor and the like, and yields a substitution volume deviation as the difference between the estimated substitution volume and the measured substitution volume for further processing. It is noted that the difference as such can be generated signed or according to amount, but is preferably a signed quantity or signal in order to provide both positive and negative deviations.

In a substitution correction section or means 116, into which the set substitution flow is input as a basic or reference value, the substitution volume deviation is processed into a substitution correction value or amount, which may then be output as a percentage of the set substitution flow, or in another suitable form representing a partial amount thereof. In the shown example, the substitution correction value or amount is determined based on a linear or proportional characteristic with clipping applied beyond some maximum point. However, there is no limitation to such particular characteristic, and a different correction amount calculation may be carried out depending on e.g. practical considerations. Again, the percentage as such can be determined signed or according to amount, but is preferably a signed quantity or signal in order to provide both positive and negative corrections.

In the following, the calculated substitution correction is combined at a point 118 with the set substitution flow to form a controlled substitution flow signal, which is corrected by the previously determined percentage or partial amount and used to control and/or drive the substitution pump 134 to properly and correspondingly retrieve substitution fluid from the substitution bag 132. A basic feedback control is accordingly realized in that the substitution fluid retrieval immediately influences the measured substitution volume, and thus also changes the substitution volume deviation as one of preconditions for the determination of the substitution correction.

Likewise, the estimated effluent volume is compared 124 to a measured effluent volume obtained from an effluent fluid scale 140 weighing substitution fluid placed into e.g. an effluent fluid bag 142 as an effluent fluid sink by the operation of an effluent pump 144. The comparison can, likewise as well, be rendered by a comparator, an adder, or suitable other logic 124 involving arithmetic operations and incorporated to this effect in some chip or microprocessor and the like, and yields an effluent volume deviation as the difference between the estimated effluent volume and the measured effluent volume for further processing. It is noted that the difference as such can be generated signed or according to amount, but is preferably a signed quantity or signal in order to provide both positive and negative deviations.

In an effluent correction section or means 126, into which the set effluent flow is input as a basic or reference value, the effluent volume deviation is processed into an effluent correction value or amount, which may then be output as a percentage of the effluent flow, or in another suitable form representing a partial amount thereof. In the shown example, the effluent correction value or amount is determined based on a linear or proportional characteristic with clipping applied beyond some maximum point. However, there is no limitation to such particular characteristic, and a different correction amount calculation may be carried out depending on e.g. practical considerations. Again, the percentage as such can be determined signed or according to amount, but is preferably a signed quantity or signal in order to provide both positive and negative corrections.

In the following, the calculated effluent correction is at a point 128 combined with the effluent flow to form a controlled effluent flow signal, which is corrected by the previously determined percentage or partial amount and used to control and/or drive the effluent pump 144 to properly and correspondingly transport effluent into the effluent bag 142. A basic feedback control is accordingly realized in that the effluent fluid retrieval immediately influences the measured effluent volume, and thus also changes the effluent volume deviation as one of preconditions for the determination of the effluent correction.

In the present embodiment, the measured substitution volume detected and output by the substitution fluid scale and the measured effluent volume detected and output by the effluent fluid scale are also input to a net removal flow calculation means, or NFR calculator, 150 which calculates a measured NFR volume from these two input values.

The measured NFR volume is a first input and an estimated NFR volume generated by predetermined integral operation on the initially set net fluid removal (NFR) flow in a calculation means 154 is a second input to a comparator, adder or suitable other logic 152 involving arithmetic operations and incorporated to this effect in some chip or microprocessor and the like. The comparator, adder or suitable other logic 152 generates an NFR deviation as the difference between the measured NFR volume and the estimated NFR volume.

The generated NFR deviation is input to an NFR comparator means 156 in which the generated NFR deviation is compared with at least one threshold value serving as an NFR alarm limit. The NFR comparator means 156 is arranged such that when the NFR deviation indicates a too low NFR, a low NFR alarm is triggered, and when the NFR deviation indicates a too high NFR, a high NFR alarm is triggered. Both alarms may be indicated and/or notified to externally of the apparatus, and may set the system into a safety state, or translate to respectively different apparatus (safety) responses depending on the issued alarm and predefined (safety) operational flows associated therewith. It is noted that the difference as the comparison result can be generated signed or according to amount, but is preferably a signed quantity or signal in order to provide both positive and negative deviations.

Next, a flow correction distribution feature and mechanism in the present embodiment will be described.

During an acute renal replacement therapy one of the most important tasks is to maintain the weight loss of the patient by controlling a target net fluid removal (NFR) rate and keeping the net fluid removal (NFR) rate (i.e. patient weight loss rate) change within a limited range around the set NFR rate in order not to cause too large weight loss rate changes for the patient.

The flow correction distribution feature in the presented embodiment avoids large fluid pump flow changes, but on the other hand corrects the NFR volume deviation as fast as possible. This is ensured by a central flow correction distributor, or distribution, means having two main tasks: a) maximizing the correction control range for a given pump in case of a deviation, and b) limiting the overall NFR rate change. Meeting these requirements allows gentle operation to the patient by allowing only a smaller correction control range and excluding high flow fluctuation in this way), while maintaining very accurate NFR and separate flow controls.

Figure 2:
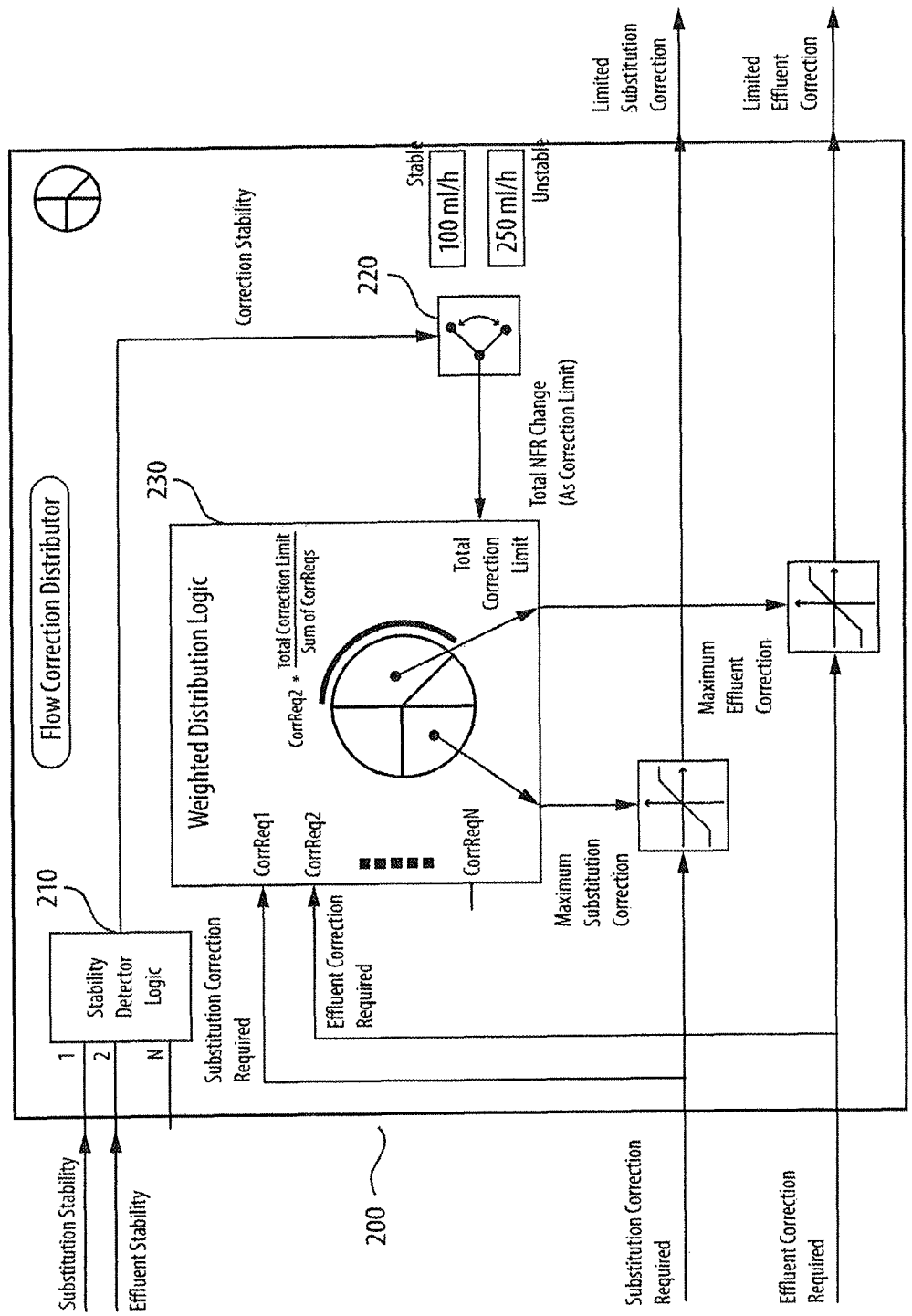
FIG. 2 schematically shows the flow correction distributor according to the preferred embodiment in greater detail.

FIG. 2 schematically shows a flow correction distribution means 200 according to the preferred embodiment in greater detail.

Generally speaking, the overall NFR rate change limit, which is the allowed total correction limit of the system, is defined by a stability detector logic means 210. If the feedback controls of all fluid flows are stable, the stability detector logic means 210 selects, via a switching means 220, a lower rate limit of e.g. 100 ml/h, while in case of any unstable control this correction limit is set to a larger rate limit of e.g. 250 ml/h in order to more quickly reach a stabilized state. The selected correction limit is input as a total correction limit into a weighted distribution logic means 230, which also gets possible flow rate correction requests (correction required) from the different pump feedback controls. The weighted distribution logic means 230 then distributes the total correction limit proportionally (as maximum corrections) among the pump feedback controls requesting any correction.

More specifically, as shown in FIG. 1, the flow correction distribution means 200 is connected, or networked, via e.g. an internal bus or harness with each feedback control means 110, 120, and further in particular with the substitution and effluent correction means 116 and 126 thereof, respectively, in a bidirectionally operating manner, wherein substitution and effluent fluid flow stability indication signals from the respective feedback controls 110, 120 are forwarded to the stability detector logic means 210, and correction required indication signals are fed into the flow correction distribution means 200. For example, such correction required indication signals may be based on a finding in the substitution and/or effluent correction means 116, 126 that a substitution and/or effluent flow correction is necessary, i.e. a calculated percentage or partial amount is other than zero.

A weighted distribution logic means 230 is provided in the flow correction distribution means, which may be based on e.g. a microprocessor system, or be part thereof or the like, without being limited thereto. The weighted distribution logic means 230 inputs the individual correction required indication signals, in the present embodiment for example one or more substitution correction required (indication) signals and an effluent correction required indication signal on the one hand, and a total correction limit indication signal on the other hand. The total correction limit has been set by the stability detector logic means 210 based on feedback control stability indication signals from each feedback control means 110, 120.

It is understood that, as mentioned above, one or more substitution pumps and, thus, one or more substitution feedback controls, one effluent pump and, thus, one effluent feedback control, and optionally other pumps with—as the case may be—associated other feedback controls may be present in the overall apparatus. The number of pumps, feedback controls, stability indication signals and correction required signals and may, thus, be generally indicated by N, as shown in FIG. 2, and accordingly, a corresponding number of inputs and outputs may be provided to means processing these N signals.

In the weighted distribution logic means 230, the set total correction limit, in the present embodiment e.g. 100 ml/h or 250 ml/h depending on the feedback control stability detection, is distributed proportionally to the individual feedback controls requiring correction (as only these transmit an active, or positive, correction required indication signal) by dividing the total correction limit by the sum, or number, of (active) correction required indication signals, and applying the result of the division as a maximum correction to the respective (active) correction required indication signals, i.e. to the signals of those pump feedback controls that request any correction. The respective correction required signals having the maximum correction applied, or superimposed or overlaid, are then fed back as limited correction signals to the respective feedback controls and correction means thereof.

In this manner, the a.m. main requirements of a) maximizing the correction control range for a given pump in case of a deviation, and b) limiting the overall NFR rate change are met in that the overall NFR rate change is limited based on the total correction amount set because a correction limitation is introduced into the correction means of the feedback controls requesting corrections, i.e. the flow correction percentage thereof can no longer exceed a certain maximum, and in that the correction control range for a given pump is maximized because corrections and/or limitations are proportionally distributed and/or applied to only those feedback controls requesting correction.

While the invention has been described with reference to a preferred embodiment and the accompanying drawings, it is understood that the present invention is not in any way limited to particular details disclosed with respect to this preferred embodiment, and that any modification readily apparent to the skilled person based on the here presented teaching is deemed to be within the scope of protection as defined by the appended claims.

The invention claimed is:

1. An acute renal replacement therapy apparatus, comprising:
   at least two feedback controls, each feedback control including:
   an estimated volume calculator configured to calculate an estimated volume based on a set flow;
   a comparator configured to compare the estimated volume with a measured volume;
   a volume deviation determining means configured to determine a volume deviation based on the comparison of the estimated and measured volumes;
   a correction calculator configured to calculate a correction amount and output a correction signal based on the determined volume deviation;
   a flow control configured to generate a controlled flow control signal based on the calculated correction amount and the set flow; and
   a feedback control output configured to output the controlled flow control signal to a pump individually associated with each feedback control in order to at least one of forward fluid from a fluid source or pull fluid into a fluid sink; and
   a flow correction distributor including:
   an input adapted to receive the correction signal from the correction calculator in each of the at least two feedback controls;
   a limited correction signal calculator adapted to calculate a limited correction signal for each of the received correction signals;
   an output adapted to output each calculated limited correction signal to the feedback control from which the underlying correction signal has been received;
   a stability detector logic means configured to receive at least two flow stability indication signals and to output a correction stability signal; and
   a switch adapted to receive the correction stability signal from said stability detector logic means and to switch, depending on the state of the correction stability signal, between a first state yielding a first net fluid removal rate correction limit for a stable condition and a second state yielding a second net fluid removal rate correction limit for a unstable condition.

2. An acute renal replacement therapy apparatus according to claim 1, wherein said flow correction distributor comprises a weighted distribution logic means including:
a correction required signal receiver configured to receive at least two correction signals from said input; and
a maximum correction amount determining means adapted to determine a weighted maximum correction amount for each of the correction signals;
wherein the flow correction distributor is configured to apply the weighted maximum correction amount determined by the weighted distribution logic means to the correction signal it has been determined for, and to output the corrected signal as the limited correction signal.

3. A acute renal replacement therapy apparatus according to claim 2, wherein said first net fluid removal rate correction limit is lower than said second net fluid removal rate correction limit, and the net fluid removal rate correction limit set by said switch is input into the weighted distribution logic means as a total net fluid removal rate correction limit indicating an applicable total correction limit.

4. An acute renal replacement therapy apparatus according to claim 3, wherein the weighted distribution logic means is configured to calculate the maximum correction amount for at least one correction signal by dividing said total correction limit by a sum of correction requests.

5. An acute renal replacement therapy apparatus according to claim 4, wherein the at least one correction signal is an effluent correction required signal.

6. An acute renal replacement therapy apparatus according to claim 1, further comprising:
a net fluid removal rate calculator configured to receive at least a first and a second measured volume signal and to calculate a measured net fluid removal volume signal based on the input first and second measured volumes;
a net fluid removal deviation calculator configured to receive said measured net fluid removal volume signal and an estimated net fluid removal volume signal and to calculate a net fluid removal deviation signal based on said measured net fluid removal volume signal and said estimated net fluid removal volume signal; and
a net fluid removal rate comparator configured to receive the calculated ret fluid removal deviation signal, to compare the calculated net fluid removal deviation signal with a threshold value yielding a net fluid removal rate alarm limit, and to trigger a high net fluid removal alarm or a low net fluid removal alarm when the obtained net fluid removal deviation is higher than said net fluid removal limit.

7. An acute renal replacement therapy apparatus according to claim 6, wherein the apparatus is configured to be set into a safety state when the high or low net fluid removal alarm is triggered.

8. An acute renal replacement therapy apparatus according to claim 1, wherein:
a first one of said at least two feedback controls is a substitution feedback control including:
as said estimated volume calculator, an estimated substitution volume calculator configured to calculate an estimated substitution volume based on a set substitution flow;
as said comparator, a first comparator configured to compare the estimated substitution volume with a measured substitution volume;
as said volume deviation determining means, a substitution volume deviation determining means configured to determine a substitution volume deviation based on the comparison of the estimated substitution volume with the measured substitution volume;
as said correction calculator, a substitution correction calculator configured to calculate a substitution correction based on the determined substitution volume deviation;
as said flow control, a substitution flow control configured to generate a controlled substitution flow control signal based on the calculated substitution correction and the set substitution flow; and
as said feedback control output, a first output adapted to output the controlled substitution flow control signal to a substitution pump forwarding substitution fluid from a substitution fluid source;
a second one of said at least two feedback controls is an effluent feedback control including:
as said estimated volume calculator, an estimated effluent volume calculator configured to calculate an estimated effluent volume based on a set effluent flow;
as said comparator, a second comparator configured to compare the estimated effluent volume with a measured effluent volume;
as said volume deviation determining means, an effluent volume deviation determining means configured to determine an effluent volume deviation based on the comparison of the estimated effluent volume with the measured effluent volume;
as said correction calculator, an effluent correction calculator configured to calculate n effluent correction based on the determined effluent volume deviation;
as said flow control, an effluent flow control configured to generate a controlled effluent flow control signal based on the calculated effluent correction and the set effluent flow; and
as said feedback control output, a second output adapted to output the controlled effluent flow control signal to an effluent pump forwarding effluent fluid into an effluent fluid sink; and
said flow correction distributor;
said input is adapted to receive, as said correction signals, a substitution correction signal from the substitution correction calculator and an effluent correction signal from the effluent correction calculator;
said limited correction signal calculator is configured to calculate, as said limited correction signal for each of the received correction signals, a limited substitution correction signal and a limited effluent correction signal based on the substitution correction signal and the effluent correction signal; and
said output is configured to output, as said each calculated limited correction signal, the calculated limited substitution correction signal to the substitution feedback control and to output the calculated limited effluent correction signal to the effluent feedback control.

9. A flow correction distribution device for use in an acute renal replacement therapy apparatus, said acute renal replacement therapy apparatus comprising:

at least an effluent pump and one or more substitution pumps and configured to control flow rates delivered by each pump based on a measured fluid weight change and a calculated estimated delivery volume, and to automatically eliminate a pump delivery deviation using respective flow rate feedback control means associated with each of said at least an effluent pump and one or more substitution pumps;

an input configured to receive correction signals calculated by add output from a correction calculator in each flow rate feedback control means;

a limited correction signal calculator configured to calculate a limited correction signal for each of the input correction signals;

an output configured to output each calculated limited correction signal to the flow rate feedback control means from which its underlying correction signal has been received;

a stability detector logic means configured to receive at least two flow stability indication signals and to output a correction stability signal; and a switch adapted to receive the correction stability signal, from said stability detector logic means and to switch, depending on the state of the correction stability signal, between a first state yielding a first net fluid removal rate correction limit for a stable condition and a second state yielding a second net fluid removal rate correction limit for an unstable condition.

\* \* \* \* \*